United States Patent [19]

Geist

[11] Patent Number: 5,767,687
[45] Date of Patent: Jun. 16, 1998

[54] SURFACE-CAPACITOR TYPE CONDENSABLE-VAPOR SENSOR

[76] Inventor: Jon Geist, 4008 Fulford St., Olney, Md. 20832

[21] Appl. No.: 791,548

[22] Filed: Jan. 31, 1997

Related U.S. Application Data

[63] Continuation of Ser. No. 757,615, Nov. 29, 1996, abandoned.

[51] Int. Cl.$^6$ .................................................. G01R 27/26
[52] U.S. Cl. ........................... 324/664; 324/663; 324/686
[58] Field of Search .................................. 324/658, 663, 324/664, 686, 689

[56] References Cited

U.S. PATENT DOCUMENTS

| | | | |
|---|---|---|---|
| 4,639,831 | 1/1987 | Iyoda | 324/689 X |
| 4,898,476 | 2/1990 | Herrmann et al. | 324/664 X |
| 5,338,826 | 8/1994 | St. Clair et al. | 528/353 |
| 5,345,213 | 9/1994 | Semancik et al. | 338/34 |
| 5,356,756 | 10/1994 | Cavicchi et al. | 430/315 |
| 5,408,381 | 4/1995 | Thoma et al. | 361/286 |
| 5,428,102 | 6/1995 | St. Clair et al. | 524/600 |
| 5,533,393 | 7/1996 | Bonne et al. | 324/663 X |

OTHER PUBLICATIONS

"Xylylene Polymers," Encyclopedia of Polymer Science and Engineering 2$^{nd}$ Ed., vol. 17, 990–1025 (1989 No Month Available).

"Parylene Conformal Coatings Specifications and Properties," (Specialty Coating Systems, IN, Aug. 1994).

"Parylene Pellicles for Space Applications" (Specialty Coating Systems, IN, Aug. 1994).

Parylene VIP™ AF-4 (Specialty Coating Systems, IN, Jan. 1996).

A.R.K. Ralston et al., "A Model for the Relative Environmental Stability . . . ;" Transducers '95—Eurosensors IX, 821–824 (Jun.1995).

C. Cornila et al., "Capacitive Sensors in CMOS Technology With Polymer Coatings", (Date and Place of Publication Unknown).

Thomas Boltshauser, "CMOS Humidity Sensors." Diss. ETH Nr. 10320 (ETH, Zurich, 1993 No Month Available) pp. i–1, 40–41, 46–53, 63–65, 72–75, 80–81.

M. Parameswaran et al., "Micromachined Thermal Radiation Emitter From a Commercial CMOS Process", IEEE ELD 12, 57–59 (Feb. 1991).

*Primary Examiner*—Glenn W. Brown

[57] ABSTRACT

Vapor-deposition polymerization films serve as vapor-sensitive dielectrics (130, 530) over surface-type capacitive electrodes (110 and 120, 510 and 520), or as protective layers (140, 142) over vapor-sensitive dielectrics (132) or flux-concentrators (150) in surface-type capacitive-electrode vapor sensors. Arrays of sensors (411–422) with different vapor-deposition polymerization films provide selectivity among different vapor species. Vapor-sensitive films (530) covering surface-type capacitive electrodes (510, 520) cointegrated with heater elements (560, 570) on thermally isolated suspended substrates (500) provide selectivity among different vapor species.

19 Claims, 9 Drawing Sheets a)

Section A-A b)

a)

b)

c)

Section C-C

SURFACE-CAPACITOR TYPE CONDENSABLE-VAPOR SENSOR

This is a continuation of Ser. No. 08/757,615, filed 1996 Nov. 29, now abandoned.

BACKGROUND-FIELD OF INVENTION

This invention relates to improvements in surface-type capacitive condensable-vapor sensors, specifically the use of 1) vapor-sensitive dielectrics or protective layers prepared by vapor-deposition polymerization, 2) variable-temperature sensors on thermally isolated substrates to distinguish among different vapor species, and 3) arrays of such sensors having different dielectric layers to distinguish among different vapor species.

BACKGROUND-DESCRIPTION OF PRIOR ART

When water vapor or any other condensable vapor is absorbed by a polymer film, the physical properties of the film, such as mass, thickness, surface resistance, volume resistance, and dielectric constant, all change. These changes, which can be detected by various means, form the basis for different types of condensable-vapor sensors. For instance, changes in the quantity of water absorbed in humidity-sensitive films can be measured as changes in 1) the resonant frequency of a surface acoustic wave or a mechanically resonant structure coated with the film, 2) the surface or volume resistance between two electrodes connected to the film, or 3) the capacitance between sandwich-electrode or interdigitated-electrode capacitors employing the film as dielectric.

In the past, the search for improved humidity-sensitive materials has been limited to those materials that have a high water-absorption capacity. The intuitive idea behind restricting the search to such materials is twofold: 1) the greater the water absorption, the greater the change in the physical parameter, so it will be easier to measure the change; 2) the greater the water absorption relative to the absorption of other condensable vapors, the lower the error caused by the absorption of other condensable vapors. Unfortunately, however, high water absorption tends to be associated with a number of humidity sensor problems such as hysteresis, non-linearity, slow response times, and non-reversible changes in properties over long periods of exposure, particularly at elevated temperature and high humidity.

Co-integration

Recently, T. Boltshauser (CMOS Humidity Sensors, *Diss. ETH Nr.* 10320, ETH Zurich, 1993, ISBN: 3-907574-01-X), incorporated herein by reference, described a new surface-type capacitive sensor consisting of a pair of inter-digitated electrodes covered with a humidity-sensitive dielectric layer and co-integrated onto an integrated-circuit (IC) chip with a signal-processing circuit. This sensor was fabricated as a sensor precursor at a commercial silicon IC foundry and post-processed into a functional sensor by adding the humidity-sensitive dielectric layer.

Due to co-integration of the signal processing circuit on the same chip with the sensor capacitor, the circuit can detect very small changes in the capacitance of the capacitor formed by the interdigitated electrode structure without interference from stray capacitance. In fact, the changes that can be detected by this circuit are much smaller than can be detected by circuits that are not co-integrated on the same chip with the sensor capacitor. This capability is further enhanced by the use of differential signal processing. Therefore, high water-absorption capacity is no longer needed to generate a signal that can be measured precisely. Furthermore, persons of ordinary skill in the art of capacitive vapor sensors know that many different polymers can be used as dielectrics to measure the concentration of water vapor and other condensable vapors.

M. Parameswaran et al. (Micromachined thermal radiation emitter from a commercial CMOS process, *IEEE Elec. Dev. Lett.* 12, 57–59, 1991), incorporated herein by reference, have shown how to thermally isolate a substrate over an etch pit in an IC chip fabricated at a commercial silicon IC foundry so that the temperature of the suspended substrate can be raised many hundreds of degrees Celsius without raising the temperature of the chip significantly. Parameswaran et al. concentrate the heater in the center of the suspended substrate. This design is not optimum because it produces the largest temperature gradients in the center of the substrate due to the fact that most of the heat loss from the substrate is by conduction through the heater leads and substrate rather than by radiation or air conduction.

U.S. Pat. No. 5,345,213 of Semancik et al. (1994) and U.S. Pat. No. 5,356,756 of Cavicchi et al. (1994) describe structures similar to those described by Parameswaran et al. in which a thermally conductive layer is added to make the temperature more uniform over the central portion of the suspended substrate, while confining the major portion of the heating to the center of the substrate where it still tends to produce a non-uniform temperature distribution. As long as the majority of the heat loss from a suspended substrate occurs by heat conduction through the heater leads or substrate, very little if any heating should be allowed to occur in the area where a uniform temperature is desired. Therefore, the heater designs of Parameswaran et al., Semancik et al., and Cavicchi et al. are less than optimum.

Foundry fabrication followed by post-processing

It is noteworthy that the precursors for Boltshauser's capacitive humidity sensors, as well as those for the thermally isolated heater structures of Parameswaran et al., Semancik et al., and Cavicchi et al., were fabricated in a completely standard process at a commercial, silicon-IC foundry. This is a major advantage: It is a very inexpensive high-volume fabrication process, which allows signal processing electronics to be co-integrated onto the same chip with no extra processing steps. Moreover, the resulting chip can be mounted and wire-bonded in a standard integrated circuit package. These advantages reduce the cost of packaging and interfacing with the system into which the sensor is to be embedded. Finally, the design, fabrication, and testing of the sensors during the R&D phase can be carried out very inexpensively through multi-project wafer services at commercial IC foundries, and the final design can be transferred to commercial production with a minimum of cost and risk.

Boltshauser converted his sensor precursor into a functional humidity sensor by depositing a thin, humidity-sensitive dielectric film over the interdigitated electrodes present in the precursor structure. This deposition was carried out as a post-processing step following wafer fabrication at a commercial silicon IC foundry as follows: Boltshauser spun a fully imidized, solvent-soluble, planarizing, negatively photo-imageable polyimide onto chips diced from the wafer fabricated at the IC foundry, and used conventional IC photolithography to remove the polyimide over the bonding pads so that the chip could be wirebonded to a header during packaging. The fact that the sensor precursor can be post-processed into a functional sensor using a simple CMOS-compatible procedure is also a big advantage of Boltshauser's sensor.

Problems with high vapor-capacity dielectrics

Boltshauser's humidity sensor was virtually ideal from the points of view of low-cost, high-volume production and system-interfacing, which suggests its adoption in a number of markets where low enough cost sensors are not currently available, as well as in existing markets. However, this sensor suffered from one potentially devastating problem. Its sensitivity to relative humidity changed substantially upon prolonged exposure to high relative humidity.

For instance, Boltshauser reports a change in sensor gain of 40 percent after six weeks at 85° Celsius and 85% relative humidity (RH). He attributed this effect to a water-induced degradation of the polymer that increased the volume of voids in a region about 30 nm thick at the air-polymer interface.

This is a potentially serious problem for use at high humidity even at lower temperatures because the results of this test are known to be a good indicator of the long-term stability of polyimide films under prolonged exposure to high humidity. In fact, this type of instability is a problem with all of the large-water-absorption capacity polymers that have been studied for use in humidity sensors in the past, and research continues for better humidity-sensitive polymers.

For instance, Ralston et al. (A. R. K. Ralston et al., A model for the relative environmental stability of a series of polyimide capacitance humidity sensors, *Transducers '95, Eurosensor IX*, Stockholm, 821–824, 1995), recently compared the long-term stability at 85° Celsius and 85% RH of a polymer called HQDEA/4-BDAF with other high-water-absorption polymers that have been used in capacitive humidity sensors. The preparation and use of HQDEA/4-BDAF in various applications including sandwich-type humidity sensors is covered in U.S. Pat. No. 5,408,381 of Thoma et al. (1995), U.S. Pat. No. 5,428,102 of St. Clair et al. (1995), and U.S. Pat. No. 5,338,826 of St. Clair et al. (1994). Thoma et al. also report the results of stability studies of HQDEA/4-BDAF. Both studies show that HQDEA/4-BDAF is more stable under prolonged exposure to high humidity than the other polymers studied, but not as stable as desirable.

While some of the recently studied polymers have better long-term stability than that of the polyimide used by Boltshauser, they are much less convenient to prepare in thin-films suitable for use in humidity sensors. Typically, they must be sprayed or cast from solutions in volatile solvents either before curing while still in the resin form or after curing.

Unfortunately, it is difficult with this type of deposition process to produce layers that are as uniform in thickness as were obtained by Boltshauser. Furthermore, without a photolithographic capability, spraying or casting will have to be carried out on chips that have already been mounted and wire bonded. This will probably be more expensive than the procedure used by Boltshauser, which can be carried out on undiced wafers. Thus, replacement of Boltshauser's polyimide with one of the more stable large-water-absorption capacity polymers will increase the cost of producing Boltshauser's humidity sensor and reduce the reproducibility from sensor to sensor, thereby increasing the cost of calibration and interfacing. This is a high cost to pay for improved long-term stability.

Many different approaches have been reported for compensating for or minimizing the problems associated with polymers having a large water-absorption capacity, but these involve trade-offs that often introduce other problems. For instance, Boltshauser showed that a field concentrator could be used with interdigitated electrodes to produce larger signals from a thinner and therefore faster responding humidity-sensitive film. (This is always true for sandwich-type capacitive sensors, but not for surface-type capacitive sensors without field concentrators due to the less ideal capacitor geometry). However, the improvement in response time was accompanied by an increase in hysteresis that Boltshauser attributed to either nuclei condensation or a decrease in stray surface resistance with increasing humidity.

Clearly, better humidity-sensitive dielectric layers are needed if all of the potential advantages of Boltshauser's capacitive sensor structure are to be realized. Fortunately, the excellent sensitivity of his sensor structure makes it possible to extend the search for better humidity-sensitive materials to polymers that have low, but not negligible, water-vapor-absorption capacity. On the other hand, the search for improved polymers can be restricted to polymers that can be applied in uniform, pin-hole free coatings with a simple and inexpensive post-processing step following fabrication of a sensor precursor at a commercial silicon IC foundry.

OBJECTS AND ADVANTAGES

Therefore the objects and advantages of this invention are (a) to use low water-absorption polymers that can be inexpensively applied in well-controlled thin films by vapor deposition polymerization as vapor-sensitive, thin-film dielectric layers for surface-type capacitive sensor structures, (b) to use polymers that can be inexpensively applied in well-controlled thin films by vapor deposition polymerization over the primary vapor-sensitive dielectrics in surface-type capacitive sensors to prevent or minimize exposure-induced degradation in the vicinity of the air-polymer interface, (c) to use polymers that can be inexpensively applied in well-controlled thin films by vapor deposition polymerization over field concentrators in surface-type capacitive sensors to eliminate or minimize hysteresis caused by condensation nuclei on the field concentrators, (d) to use polymers that can be inexpensively applied in well-controlled thin films by vapor deposition polymerization over field concentrators in surface-type capacitive sensors to eliminate or minimize hysteresis and non-linearity caused by humidity-sensitive surface-resistance paths to the field concentrators.

(e) to co-integrate a set of surface-type capacitive sensors of the type described above, where each sensor has a different polymer-dielectric layer, to provide different patterns of response over the set for different vapors thereby allowing different vapors to be distinguished from one another.

(f) to use surface-type capacitive sensors of the type described above, where each sensor is located on a thermally isolated suspended substrate having a heater and temperature sensor to measure the temperature at which different condensable vapors in a mixture of vapors desorb out of (absorb into) the polymer dielectric during heating (cooling) of the thermally isolated suspended substrate as a way to distinguish different condensable vapors from one another, (g) to fabricate precursors co-integrated with control/signal-processing circuits for the type of sensor described above at commercial IC foundries in standard IC processes for conversion into functioning condensable-vapor sensors by postprocessing with vapor-deposition polymerization.

Further objects and advantages will become apparent from a consideration of the ensuing description and drawings.

DRAWING FIGURES

FIGS. 1a, 1b, and 1c show the chemical structures of different xylylene compounds.

FIGS. 4a and 4b compare the geometry of a typical pair of spiral electrodes with that of a typical pair of interdigitated electrodes.

Figure 5:
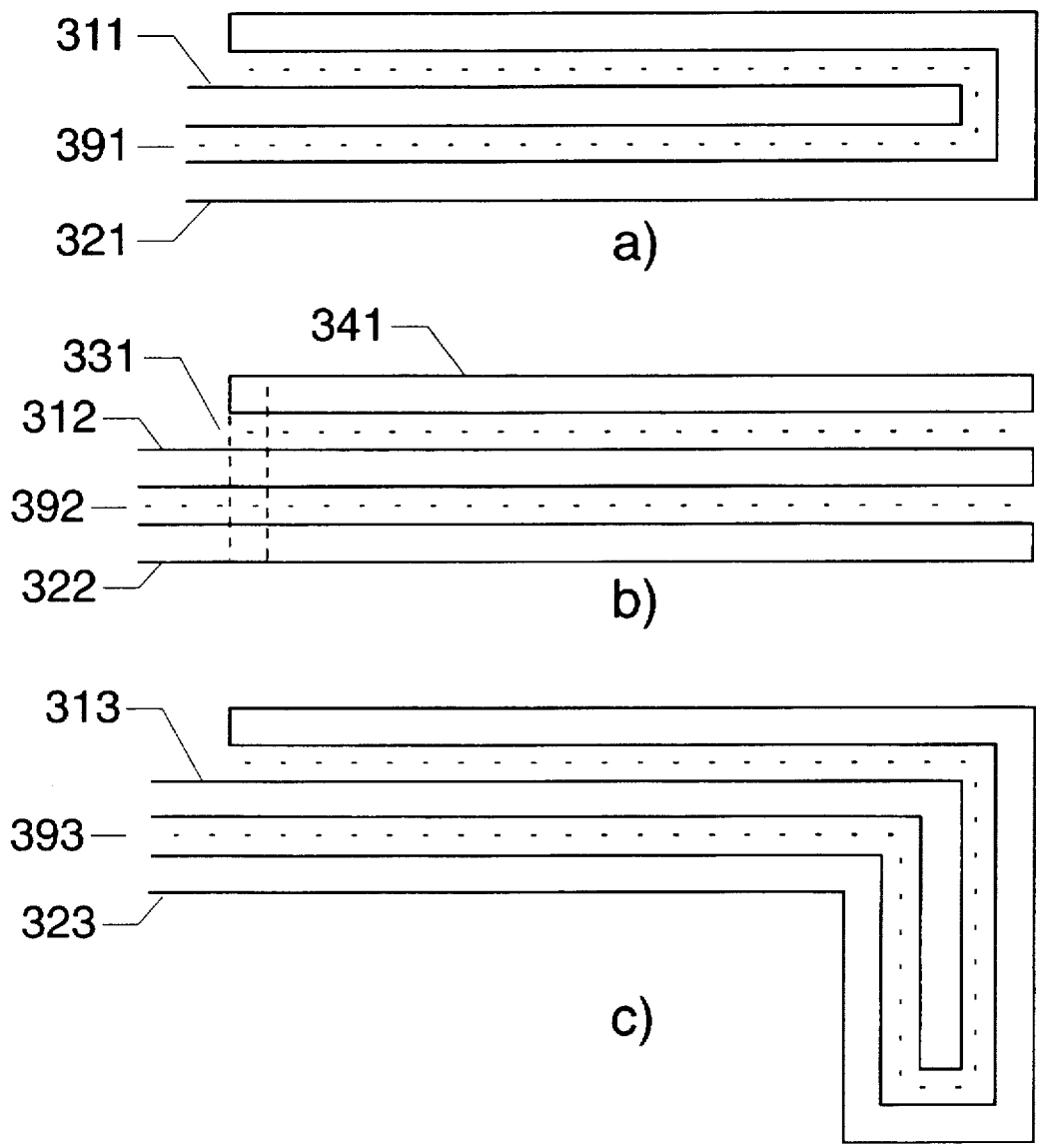

FIGS. 5a, 5b, and 5c show some very simple interdigitated electrode.

Figure 6:
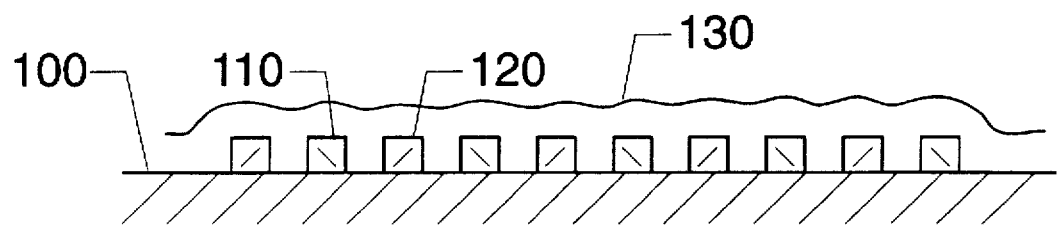
Figure 6:
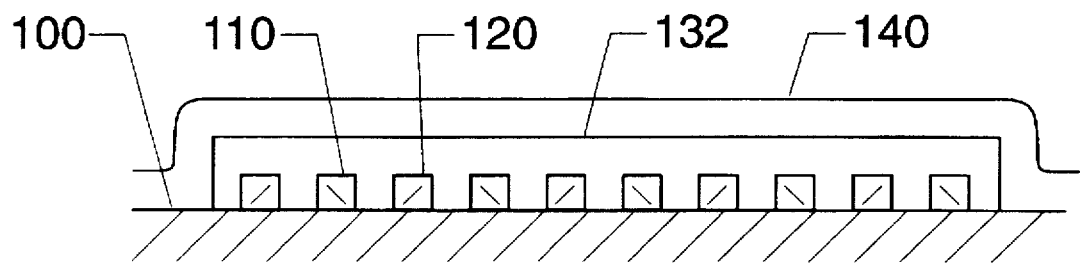
Figure 6:
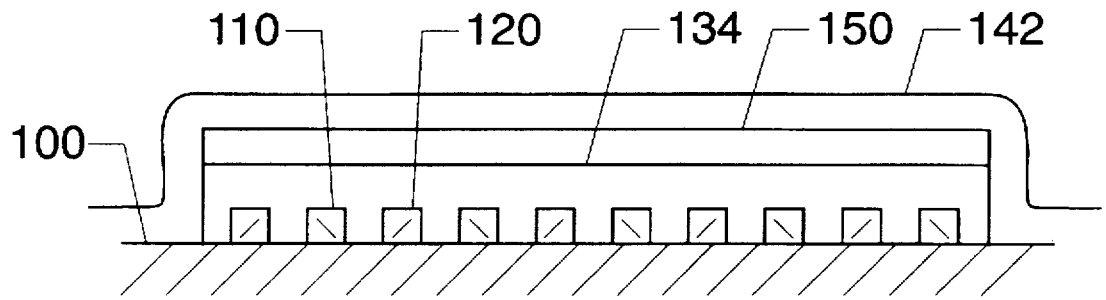

FIGS. 6a, 6b, and 6c show cross sections of capacitive vapor sensors employing different layers.

Figure 7:
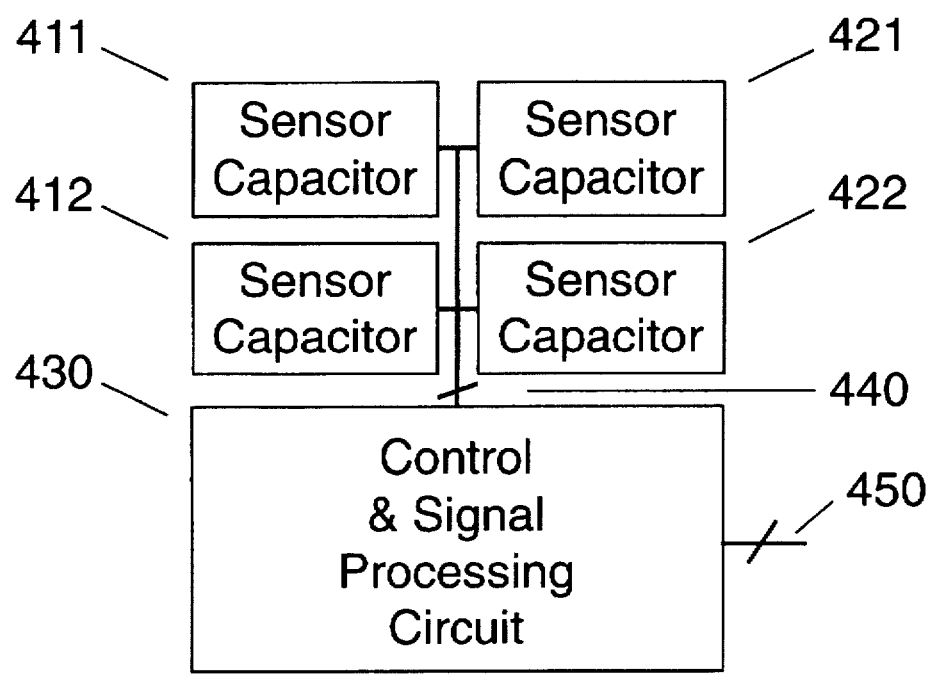

FIG. 7 is a schematic illustration of an array of surface-capacitor condensable-vapor sensors cointegrated with a signal processing circuit.

Figure 8:
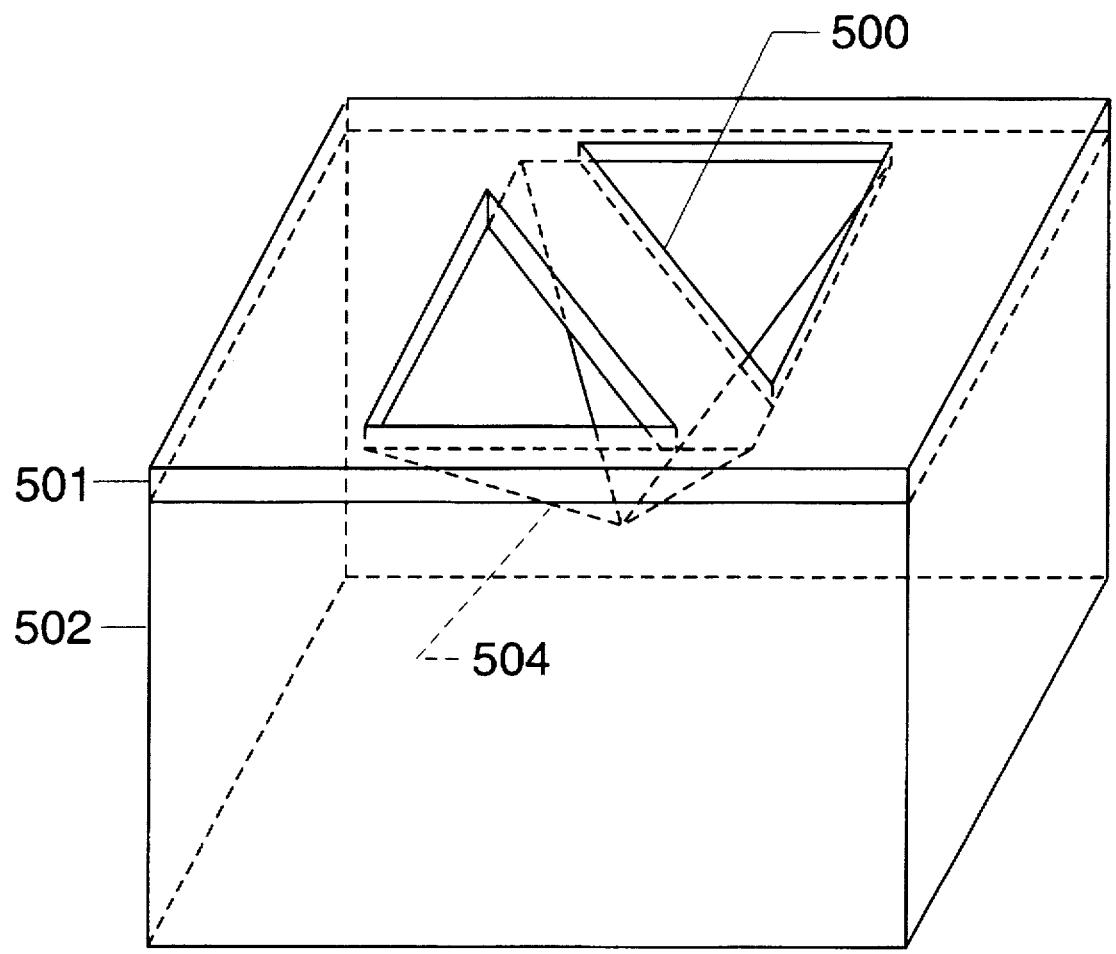

FIG. 8 is a perspective view of a silicon-dioxide substrate suspended over an etch pit in a silicon chip to provide thermal isolation of the substrate from the chip.

FIGS. 9a and 9b show a top view and a cross section of a silicon chip having a vapor-sensitive, interdigitated-electrode capacitor cointegrated with two heater and two temperature sensors onto a substrate suspended over an etch pit in the chip.

DESCRIPTION: FIGS. 1a–9b

FIGS. 1a, 1b, and 1c show the chemical structures of di-para-xylylene, para-xylylene, and one structural unit of the polymer, linear poly(paraxylylene), respectively. Linear poly(para-xylylene) will be referred to here as poly(p-xylylene).

When atoms or groups of atoms are substituted for one or more of the hydrogen atoms at the 2, 3, 5, or 6 positions in the aromatic ring in a substantial fraction of the structural units of poly(p-xylylene), which is shown in FIG. 1c, the product is a substituted poly(p-xylylene). The term, polyxylylene polymer, will be used to refer to poly(p-xylylene) and substituted poly(p-xylylene) polymers collectively.

When there is on average one chlorine atom substituted for one ring hydrogen atom per structural unit, the resulting substituted poly(p-xylylene) will be called poly(p-chloroxylylene). When there are on average two chlorine atoms substituted for two ring hydrogen atoms per structural unit, the resulting substituted poly(p-xylylene) will be called poly(p-dichloroxylylene). When a fluorine atom has been substituted for a hydrogen atom at most or all of the 2, 3, 5, and 6 positions in most or all of the aromatic rings, the resulting substituted poly(p-xylylene) will be called poly(p-tetrafluoroxylylene).

Figure 1:
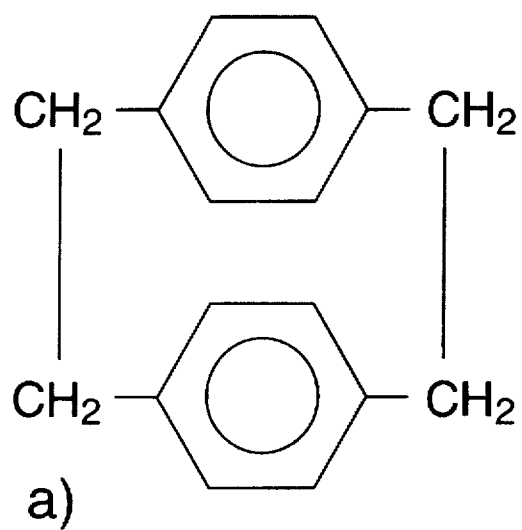
Figure 1:
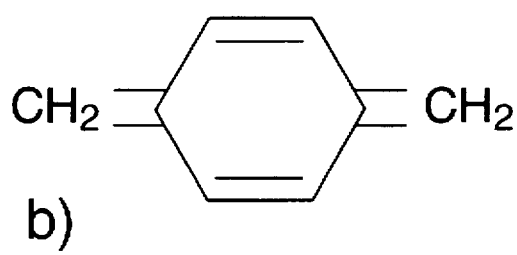
Figure 1:
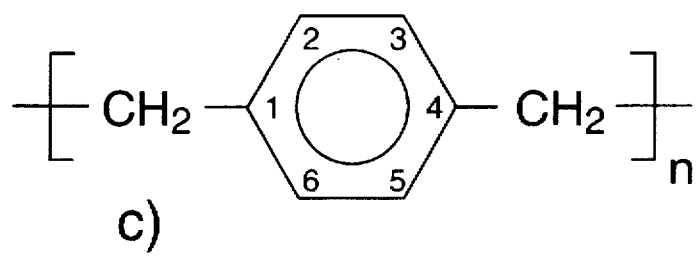
Figure 2:
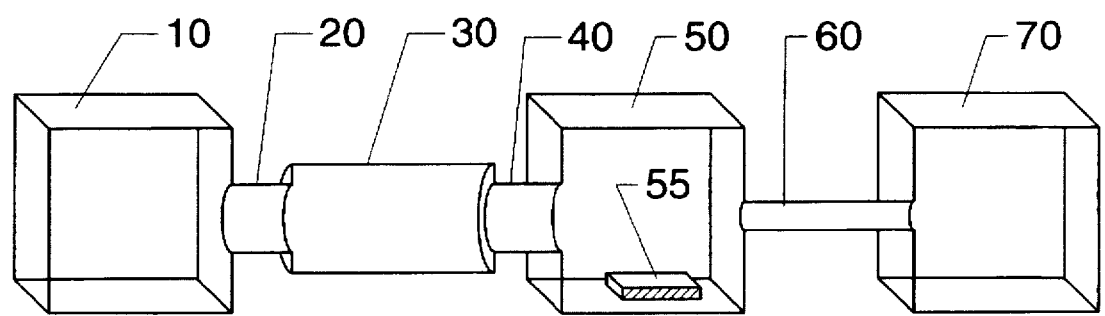
FIG. 2 shows a cut-away view of the main components of a vapor-deposition polymerization system.
Figure 3:
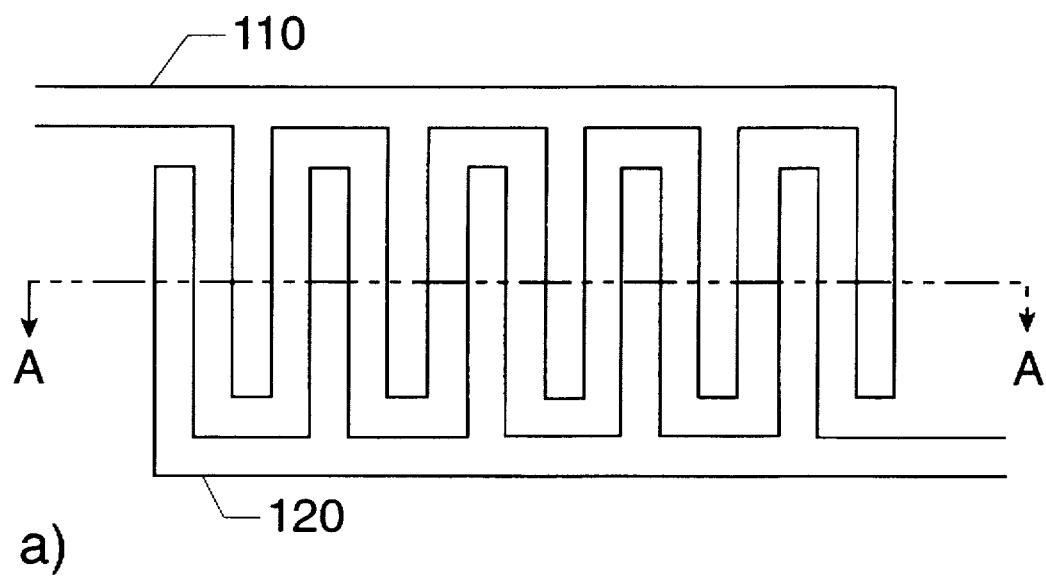
FIGS. 3a and 3b show a top view and cross section of a precursor for a condensable-vapor sensor.
Figure 3:
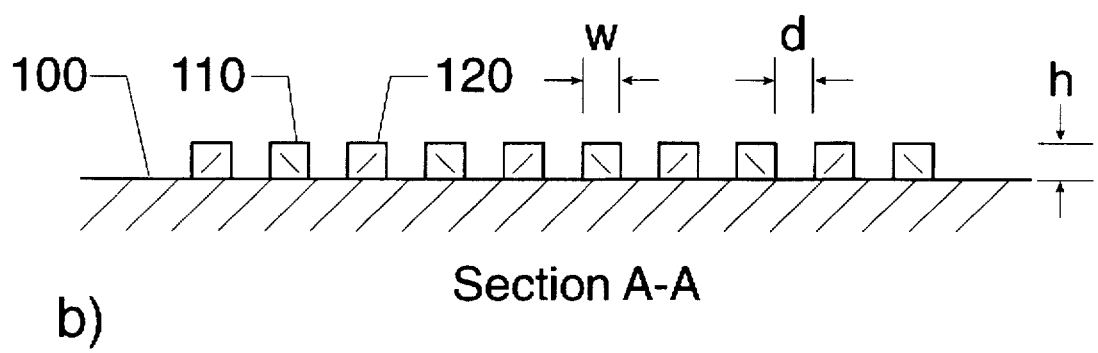

FIG. 2 is a simplified cut-away view of a vapor deposition polymerization system. A vaporization chamber 10 is connected by a tube 20 to a reaction chamber 30 that is connected by a tube 40 to a deposition chamber 50. The deposition chamber 50, which is connected to a vacuum pump 70 through a tube 60, contains a condensation stage 55.

FIG. 3a shows a top view and FIG. 3b shows a cross section along a dashed line A of a pair of interdigitated electrodes for a condensable-vapor sensor precursor such as can be fabricated at a commercial silicon-IC foundry. An electrically-insulating substrate 100 supports two interdigitated electrodes 110 and 120 of height h, width w, and separation distance d. The capacitance of the capacitor consisting of the two electrodes 110 and 120 depends primarily upon the space between the two electrodes. The area between a pair of electrodes when viewed from the top of the chip as in FIG. 3a will be called the active area of the pair.

FIG. 4a shows a typical geometry for a pair of spiral-electrodes 210 and 220. The active area of the pair is the area 290 marked by dots. FIG. 4b shows a typical geometry for a pair of interdigitated electrodes 310 and 320. The active area of the pair is the area 390 marked by dots.

FIGS. 5a, 5b and 5c show some very simple interdigitated electrode geometries. FIG. 5a shows an electrode 311 that is partially surrounded by a second electrode 321. The active area 391 between the electrodes 311 and 321 is shown dotted for clarity. FIG. 5b shows an electrode 312 that is partially surrounded by a second electrode comprised of two electrode segments 322 and 341 that are connected electrically by a third electrode segment 331 which is insulated from the electrode 312 by a conventional insulating layer. The active area 392 between the electrode 312 and the electrode made up of the segments 322, 331, and 341 is shown dotted for clarity. FIG. 5c shows a slightly more complex pair of interdigitated electrodes than shown in FIG. 5a. An electrode 313 is partially surrounded by a second electrode 323. The two electrodes 313 and 323 run parallel to each other, and both make a right angle turn together. The active area 393 between the electrodes 313 and 323 is shown dotted for clarity.

FIG. 6a shows a cross section of a condensable-vapor sensor made from the sensor precursor shown in FIG. 3b. The electrodes 110 and 120 are encapsulated between the electrically-insulating substrate 100 and a polyxylylenepolymer dielectric layer 130. FIG. 6b shows a cross section of a second condensable-vapor sensor made from the sensor precursor of FIG. 3b. Here the electrodes 110 and 120 are encapsulated between the electrically-insulating substrate 100 and a vapor-sensitive sensor dielectric 132, which need not be a polyxylylene polymer, but the vapor-sensitive dielectric 132 is covered by a protective layer of a polyxylylene polymer 140. FIG. 6c shows a cross section of a third condensable-vapor sensor made from the sensor precursor of FIG. 3b. Here the electrodes 110 and 120 are encapsulated between the electrically-insulating substrate 100 and a vapor-sensitive sensor dielectric 134, but the vapor-sensitive dielectric 134 is covered by a field concentrator 150, and the entire structure is covered with a protective layer of a polyxylylene polymer 142.

FIG. 7 is a schematic diagram of a condensable-vapor sensor incorporating a set of sensors of the type illustrated in the preceding figures. Each sensor in the set is called a sensor element to distinguish between the individual sensors that make up the set and the sensor that includes all of the sensors in the set. A control/signal-processing circuit 430 is connected electronically by a fanout of lines 440 to four different surface-type capacitive vapor sensor elements 411–422 configured as an array. The output of the circuit 430 is sent to other conventional circuits by a bus 450.

FIG. 8 shows a perspective view of a silicon dioxide layer 501 from which a thermally isolated substrate 500 is suspended over a pit 504 etched in a silicon chip 502. The suspended substrate shown in the figure is a bridge-type suspended substrate. Cantilevers and membranes are also possible. FIGS. 9a and 9b show a top view in a) and cross section in b) of two electrical heaters 560 and 570, two resistive temperature sensors 580 and 590, and a pair of interdigitated electrodes 510 and 520 supported by the substrate 500 of FIG. 8. The substrate 500 is suspended over the etch pit 504 in the silicon chip 502. The substrate 500, the electrodes 510 and 520, the temperature sensors 580 and 590, and the heaters 560 and 570 are covered by a conformal coating 530 of a polyxylylene polymer. The electrodes 515 and 525 serve no electrical purpose. All that they do is make the heat transfer from the suspended structure more uniform when heated by the heaters 560 and 570.

OPERATION: FIGS. 1–8

Vapor deposition polymerization

Poly(p-xylylene) is the prototypical polymer that can be prepared by vapor-deposition polymerization (VDP). Di-para-xylylene, which is a colorless, exceptionally stable and chemically inert, highly crystalline solid at room temperature, is the starting material for this VDP process. The chemical structure of di-para-xylylene is shown in FIG. 1a.

FIG. 2 is a cut-away view of the major components of a poly(p-xylylene) VDP apparatus. A sample of di-para-xylylene is heated to around 200° Celsius in the vaporization chamber 10. Under these conditions, it is in equilibrium with a vapor phase at a pressure of about 150 Pascals. This vapor phase passes by diffusion from the vaporization chamber 10 through the tube 20 into the reaction chamber 30 where it is heated to around 680° Celsius. At this temperature, it thermally cleaves into two para-xylylene molecules, each of which has the structure shown in FIG. 1b.

The para-xylylene vapor, which is stable in the gas phase at a pressure of 50 Pascals maintained by the vacuum pump 70, passes by diffusion from the reaction chamber 30 through the tube 40 into the condensation chamber 50. Here some of the para-xylylene vapor condenses and spontaneously polymerizes on the condensation stage 55, which is maintained at room temperature, and on any objects that are mounted on the condensation stage. The resulting polymer forms a conformal coating of high molecular weight poly (p-xylylene), whose structural unit is shown in FIG. 1c.

Conformal layers of other polyxylylene polymers can be prepared by vapor-deposition polymerization by similar means. When a poly(p-xylylene) coating is prepared by VDP from a dimer produced by Union Carbide Corporation, it is called Parylene N. When a poly(p-chloroxylylene) coating is prepared by VDP from a dimer produced by Union Carbide Corporation, it is called Parylene C. When a poly(p-dichloroxylylene) coating is prepared by VDP from a dimer produced by Union Carbide Corporation, it is called Parylene D. When a poly(p-tetrafluoroxylylene) coating is prepared by Specialty Coatings Systems, Inc., it is called Parylene VIP™ AF-4.

Advantages of polyxylylene polymers

Polyxylylene polymers have many properties recommending their use in humidity and other type of condensable vapor sensors. For instance, 1) they have low water-absorption capacity, 2) they are insoluble in all organic solvents below about 150° Celsius, and 3) hydrolytic degradation is chemically impossible.

Equally important, conformal, pin-hole free coatings of polyxylylene polymers can be prepared by the simple, inexpensive VDP process described above. This process is particularly well suited as a post-processing step to convert a sensor precursor that was fabricated on a chip at a silicon IC foundry into a functional sensor chip. This makes polyxylylene polymers excellent choices for use in condensable-vapor sensors that are co-integrated with integrated circuits.

So far, it has not been possible to carry out conventional solvent-based photolithography on polyxylylene polymers. This is not a problem, however, because other photolithographic procedures may be used. For instance, it is possible to plasma etch polyxylylene while protecting the areas on which the polyxylylene is to remain with photoresist. Lift off with standard photoresists is another photolithographic option.

VDP polyxylylene coatings can be applied to ICs at the wafer, chip, or package level. In the first case, one or more wafers are loaded into the VDP deposition equipment for coating before the wafers are diced. In the second case, waffle-packed or tape-packed chips are loaded into the VDP coating equipment after dicing, but before packaging. In the third case, packages in which IC chips have been mounted and wire bonded (and maybe even tested) are loaded into the VDP deposition equipment for coating. Of course, the package must be open to the extent that the xylylene vapor can reach the chip by diffusion for the last option to be useful. Those of ordinary skill in the IC design and fabrication art know how and where to add photoresist deposition and photolithography steps to one or more of these simple VDP processes to use plasma etching or lift off to pattern the polyxylylene deposited during the VDP process, if required as might be the case for wirebonding. On the other hand, if the polyxylylene coating is thin enough, then the electrical connections to the chip can be made by wirebonding through the polyxylylene coating with a conventional wire bonding apparatus.

The main disadvantage of polyxylylene polymers is that they oxidize significantly at rather low temperatures. For instance, polyxylylene loses half its tensile strength in ten years in air at 60° Celsius due to oxidation. For applications in which this might be a problem, substituted polyxylylene polymers that oxidize much more slowly at any given temperature, such as poly(pchloroxylylene), are available. For instance, it takes ten years in air at 80° Celsius to oxidize poly(p-chloroxylylene) enough for it to lose half its tensile strength, while it takes well over 100 years in air at 60° Celsius.

Other vapor-deposition polymers

Those of ordinary skill in the art of vapor deposition will see that VDP can be used to deposit polymers other than polyxylylenes provided certain conditions are met:

- There must be a stable starting material that can be shipped and stored for long periods of time without degradation. The starting material can be a gas, liquid, solid, or mixture containing components in any or all of these phases. If the starting material is a mixture, then the components need not be stable when mixed, only when stored separately.
- The starting material must give off a vapor in the vaporization chamber 10 shown in FIG. 2, either as a reaction product or as a result of some physical process like heating or irradiation.

The vapor leaving the vaporization chamber 10 must either polymerize upon condensation on objects held at the temperature of the condensation stage 55, or it must be possible to convert this vapor into a vapor that will polymerize under these conditions as a result of some physical process like heating or irradiation. Any polymer that is deposited by vapor deposition polymerization will be called a vapor deposition polymer.

Those of ordinary skill in the art of vapor deposition will also see that the reaction chamber 30 is not needed if the vapor given off by the starting material polymerizes upon condensation. The reaction chamber 30 is needed only when the vapor given off by the starting material does not polymerize upon condensation. In this case, the reaction chamber is used to convert the vapor given off by the starting material into a vapor that does polymerize upon condensation. In any case, it is possible, if necessary, to heat the walls of the vaporization chamber 10, the deposition chamber 50, and other chambers and tubes to a high enough temperature to prevent condensation and polymerization of the vapor on these surfaces. These temperatures are 30° C., 90° C., and 130° C. for poly(p-xylylene), poly(p-chloroxylylene), and poly(p-dichloroxylylene), respectively.

So far, not many polymers for which VDP is practical or even possible have been identified. Nevertheless, those of ordinary skill in the art of vapor deposition processes are able to build the equipment needed for VDP deposition of any polymers that satisfy the above conditions after reference to the pertinent literature. On the other hand, commercial deposition services are an option for Parylene polymers.

Not only is VDP a very convenient process for post-processing sensor precursors into functional sensors, but it also provides important advantages with respect to coating quality when compared to other methods of depositing polymer coatings. Other means of depositing polymer coatings include casting and spraying from solution in a volatile solvent. It is very difficult to obtain thin coatings of uniform thickness with these techniques. Spin coating is another way that many polymers can be applied. While, it produces more uniform thickness coatings that spraying and casting, it tends to produce coatings with planar top surfaces rather than conformal coatings, and does not work well for very thin coatings. On the other hand, VDP is a conformal process in which uniform thickness, pin-hole free coatings are readily produced, even in very thin layers. In fact, among all of the common polymer coating processes, VDP provides the most uniform thickness coatings.

Surface-type capacitors

FIGS. 3a and 3b show top and cross-section views of a typical surface-type capacitor for a condensable-vapor sensor precursor such as can be fabricated at a commercial IC foundry. The precursor shown consists of a pair of inter-digitated electrodes 110 and 120 of width w and height h deposited on an insulating substrate 100 and separated by an inter-electrode distance d. In reality, there is a non-zero capacitance between any two electrically conductive structures. Therefore, the goal in the design of two electrodes for use as a surface-type capacitor is to maximize the capacitance between the two electrodes while minimizing the capacitance to all other electrically conductive structures. This imposes five, not completely consistent, requirements:

maximize the height h of the electrodes,
minimize the distance d between the pair of electrodes,
minimize the widths w of each electrode,
maximize the length of the active area between the two electrodes
minimize the overall area occupied by the two electrodes,
maximize the minimum distance from the two electrodes to any other conducting structures.

To these requirements must be added some constraints. First, the height of each material layer is fixed by the foundry process being used. Second, there is a minimum electrode width and minimum electrode spacing available from the foundry process being used.

It is the capacitance between the electrodes 110 and 120 that is the quantity of interest, but only after post-processing of the sensor precursor into a functional sensor by the deposition of a vapor-sensitive dielectric layer over the pair of electrodes. The primary contribution to the capacitance comes from the active area (the region between the electrodes as seen from the top of the chip), but significant contributions also come from the substrate and the region above the electrodes (as seen in cross section) due to fringing-field effects.

Figure 4:
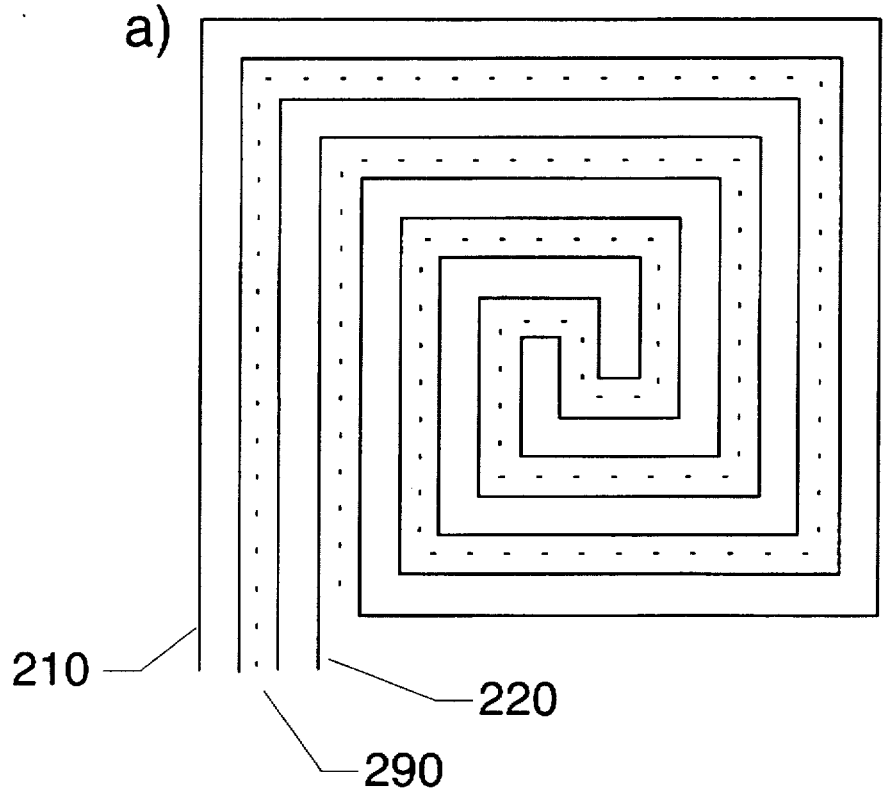
Figure 4:
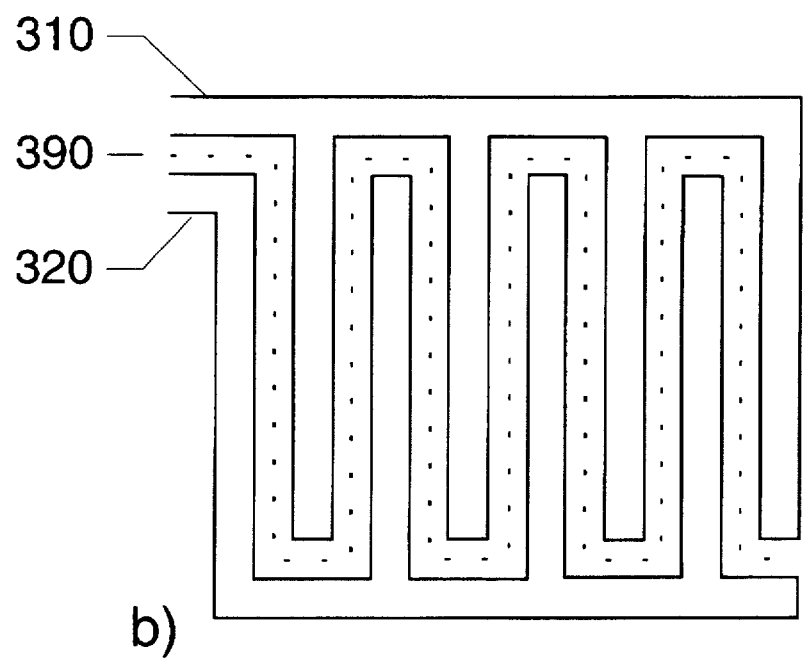

Different surface-capacitor electrode geometries have different capacitances per unit area for fixed electrode line width w, height h, and spacing d. FIG. 4 illustrates two efficient geometries. FIG. 4a shows a typical pair of spiral electrodes and FIG. 4b shows a typical pair of interdigitated electrodes. The active areas are shown dotted in these figures for clarity.

Persons of ordinary skill in IC layout are able to modify these geometries to accommodate different external constraints such as connections to the electrodes. For instance, the electrodes of FIG. 4b run parallel, while those in FIG. 3a go in opposite directions, as they exit the interdigitated portion of the structure. The choice between these and other alternative geometries will depend upon the geometry of the circuit to which the electrodes are connected.

Other geometries involving combinations of interdigitation and double spirals can be used to enhance the capacitance of surface-type capacitors. FIGS. 5a, 5b, and 5c show some very simple interdigitated electrode geometries. These and similar geometries may prove useful in squeezing a pair of interdigitated electrodes into free space between other structures such as circuit elements.

The point is that any geometry that surrounds one electrode with a second electrode without including any other electrodes is either a pair of interdigitated electrodes, a pair of spiral electrodes, or a combination of the two. From the point of view of inter-electrode capacitance, even two serpentine electrodes running parallel to each other are interdigitated. On the other hand, a pair of serpentine electrodes is an inefficient capacitive structure because there is always another pair of interdigitated electrodes having the same electrode width, spacing, and height, as well as the same capacitance that has a substantially smaller surface area.

Those of ordinary skill in the art of IC design will note that the interdigitated-electrode capacitive structure shown in FIGS. 3a and 3b can be fabricated in standard CMOS and standard bipolar IC processes. In either case, the substrate 100 could be made from a thermal oxide layer, which is available in all standard processes, and the electrodes 110 and 120 could be made from a metal layer, which is available in all standard processes. Other choices could also be made depending upon what other layers are available in different standard processes. For instance, most standard CMOS processes have at least one polysilicon layer. When available, either or both electrodes could be made from this layer. Similarly, other insulating layers that may or may not be available in any given standard process such as nitrides, mixed oxy-nitrides, and glasses could also be used in the substrate. Finally, those skilled in the art of IC design will see that the surface-type capacitor of FIGS. 3a and 3b is a sensor precursor for any sensor having a dielectric layer between the electrodes 110 and 120 that is added, not as part of the IC fabrication process, but as a post-processing step.

Vapor-sensitive sensors based on polyxylylene films

First, consider the preferred embodiment of a humidity sensor shown in FIG. 6a. The polyxylylene polymer layer 130 absorbs a quantity of water that is proportional to the relative humidity (RH) of the air to which the physical structure is exposed. Thus, the capacitance of the interdigitated-electrode capacitor structure, which consists of the layer 130, the substrate 100, and the electrodes 110 and 120, depends upon the RH of (and the concentration of any other condensable vapors in) the air surrounding the sensor.

This change in capacitance can be measured by a circuit similar in function to that described by Boltshauser. Unless the area covered by the interdigitated electrodes 110 and 120 is very large, it will be necessary to co-integrate the sensor structure and circuit onto the same IC chip to obtain satisfactory signal-to-noise ratio and freedom from effects of stray capacitance.

Since the deposition of polyxylylene-polymer coatings is an almost ideal post-processing step for IC wafers and packages, tight co-integration of sensors employing polyxylylene polymers with appropriate signal-processing circuits on the same chip is readily and inexpensively achieved. Those of ordinary skill in the art of IC design and fabrication will know how to design such a cointegrated sensor precursor and circuit based on what is taught here and by Boltshauser.

Polyxylylene polymers tend to have low water-absorption capacities. For instance, poly(p-xylylene) has a water-absorption capacity of 0.01% by weight at 100% RH, and poly(p-xylylene) has a water-absorption capacity of 0.06% by weight at 100% RH. By comparison, the polyimide used by Boltshauser has a water-absorption capacity of 5.6% by weight at 100% RH.

Because the water-absorption capacity of the polyxylylene polymer layer 130 is low, there will be negligible hysteresis in the capacitance-humidity characteristic of the sensor structure. Furthermore, since hydrolytic degradation of polyxylylene polymers is chemically impossible, there will be no change in sensitivity of this sensor due to humidity-induced changes in the humidity-sensitive polyxylylene layer. Finally, since these polymers are insoluble in all organic solvents below about 150° C., the possibility of degradation due to prolonged exposure to solvent and other vapors is also greatly reduced.

The dielectric constant of poly(p-xylylene) changes very little with temperature between 0° and 100° C., so that little if any temperature compensation will be needed if this polymer is used as the dielectric layer 130 in a condensable-vapor sensor of the type shown in FIG. 6a. On the other hand, the dielectric constant of poly(p-chloroxylylene) increases by over one third over this same temperature range, so temperature compensation will probably be required if the sensor of FIG. 6a is to be used over a wide temperature range. In either case, a temperature compensation circuit can be co-integrated with the humidity sensor structure on the sensor chip. Those of ordinary skill in the art of IC design and ASIC fabrication will know how to design such a circuit for co-integration with the sensor precursor.

It might be supposed that the sensitivity to RH of a capacitive-sensor structure employing poly(p-chloroxylylene) would be only 1% of that of an identical sensor structure employing the polyimide used by Boltshauser since the water-absorption capacity of the former is only 1% of that of the latter. However, this is not the case. The sensitivity to humidity of a capacitive sensor structure does not scale linearly with the water-absorption capacity of the capacitor dielectric. This fact is well illustrated by results reported by Ralston et al.

These authors compare the performance of a number of polymers with large water-absorption capacities as humidity-sensitive dielectrics in sandwich-electrode, capacitive-sensor structures. All of these sensor structures had the same area, but the thickness of the humidity-sensitive layers varied a little from material to material.

Ralston et al. report 93% as the ratio for the sensitivity of a structure using the polymer HQDEA-4BDAF to the sensitivity of a structure using the polymer Upilex®R. This ratio becomes 78% when corrected for the actual layer thicknesses used in the sensor structures. On the other hand, the ratio of the water-absorption capacities of the two polymers is only 19%. Thus an eighty percent reduction in water-absorption capacity of the humidity-sensitive layer was accompanied by only a twenty percent reduction in sensitivity. Even including corrections for the different dielectric constants of the polymers fails to produce ratios that scale as expected.

Therefore, it will probably be necessary to determine the sensitivity of a humidity-sensor employing any given polyxylylene polymer by experiment rather than by extrapolation from its water-absorption capacity and the measured sensitivity of a similar sensor coated with another polymer of known water-absorption capacity. Persons of ordinary skill in the polymer-based condensable-vapor sensor art will see that polyxylylene polymers can be used in the same structure described above to sense other condensable vapors besides water vapor due to the non-selectivity of the absorption of vapors by polymers.

Prevention of humidity-induced degradation

Now consider the preferred embodiment of a humidity sensor that is shown in FIG. 6b. In this case, the humidity-sensitive layer 132 is the polyimide used by Boltshauser and the protective film 140 is poly(p-dichloroxylylene) whose thickness is at least 30 nm, but not more than 100 nm. In this embodiment, the protective film of poly(p-dichloroxylylene) 140 passes water vapor to the humidity-sensitive dielectric layer 132 which absorbs a quantity of water that is proportional to the RH of the air to which the physical structure is exposed. Thus, the capacitance of the interdigitated-electrode structure, which consists of the dielectric layer 132, the substrate 100, and the electrodes 110 and 120, depends upon the RH of the air surrounding the sensor.

The protective film 140 of poly(p-dichloroxylylene) assures that there is no polyimide within 30 nm of the air-polymer interface to degrade as a result of prolonged exposure to high humidity. Furthermore, the poly(pdichloroxylylene) that forms the air-polymer interface is not affected by prolonged exposure to high humidity and oxidizes very slowly even at 85° C.

As a result, the gain of this sensor structure will be much more stable during exposure to 85% RH and 85° C., as well as prolonged exposure to high humidity at the lower temperatures encountered in typical humidity sensor applications than was the structure described by Boltshauser.

Another advantage of poly(p-dichloroxylylene) is that pin-hole free films of this material can be prepared with thicknesses as low as 30 nm. Thus a poly(p-dichloroxylylene) film of less than 100 nm will be sufficient to prevent humidity induced degradation near the exterior surface of polyimide. Since the required thickness of the humidity-sensitive polyimide, which is of the order of a few micrometers, is much larger than 100 nm, neither the sensitivity nor the time constant of the sensor structure will change significantly following deposition of the protective film 140 of polyxylylene polymer on the polyimide humidity-sensitive layer 132. Finally, a 30 nm film of parylene is so thin that the chip can be wirebonded through the film. Thus, this film adds a negligible cost to Boltshauser's sensor if all of the postprocessing is done at the wafer level, which is certainly the most inexpensive way to post-process Boltshauser's precursor into a functional sensor.

Those of ordinary skill in the vapor-sensor art will see that poly(p-dichloroxylylene) and other polyxylylene polymers can be used as protective films to prevent near-surface degradation with any type of vapor-sensitive layer, not just those made with the type of polyimide used by Boltshauser, and in any type of condensable-vapor sensor, not just humidity sensors.

Protecting flux concentrators from the effects of humidity

Finally, consider the preferred embodiment of a humidity sensor shown in FIG. 6c. In this case, the dielectric layer 134 is the polyimide used by Boltshauser, the protective film 142 is poly(p-dichloroxylylene), and the field concentrator 150 is permeable to the vapors of interest and has a high-electrical conductivity.

In this embodiment, the protective film of poly(p-dichloroxylylene) 142 passes water vapor to the field concentrator 150, which in turn passes water vapor to the dielectric layer 134 which absorbs a quantity of water that is proportional to the RH of the air to which the physical structure of FIG. 6c is exposed. Thus, the capacitance of the interdigitated-electrode structure, which consists of the field concentrator 150, the dielectric layer 134, the substrate 100, and the electrodes 110 and 120, depends upon the RH of the air surrounding the sensor.

Without the protective film 142 of poly(p-dichloroxylylene), water can condense onto condensation nuclei on the field concentrator at high humidity. If the condensed water fails to evaporate as the humidity is lowered as often happens in the presence of condensation nuclei, excess water, which is in equilibrium with the water associated with the condensation nuclei will be retained in the humidity-sensitive layer under the field concentrator. The result is hysteresis. The addition of the protective film of poly(p-dichloroxylylene) prevents water from condensing on the field concentrator thereby eliminating the possibility of hysteresis from this effect.

Also, without the protective film 142 of poly(p-dichloroxylylene), water can condense on the surface of the humidity-sensitive polymer 134 adjacent to the edge of the field concentrator. This can lower the surface resistance from the field concentrator 150 to other electrically conductive structures on the sensor as the humidity increases, which can result in non-linearity or hysteresis. The addition of the protective film 142 of poly(p-dichloroxylylene) prevents water from condensing on any surfaces that are in electrical contact (through humidity-dependent surface conductance) with the field concentrator 150, thereby preventing non-linearity and hysteresis from this source.

Multiple surface-type capacitor vapor-sensor elements for selectivity

FIG. 7 illustrates the co-integration of a number of surface-type capacitive sensors and a signal processing circuit into a composite condensable-vapor sensor that displays selectively among different vapors in mixtures of vapors and other gases. For the purposes of this discussion, it will be more convenient to refer to the individual condensable-vapor sensors as condensable-vapor sensor elements and to refer to the composite condensable-vapor sensor that is made up from the individual elements as a condensable vapor-sensor. Nevertheless, the condensable-vapor sensor elements are identical to what has been referred to as a condensable-vapor sensor up to now.

Polymers are not selective for any single vapor, but absorb some quantity of almost any vapor. This means that the signal coming out of a condensable-vapor sensor cannot be assigned to some specific vapor unless it is known a priori that no vapor except that vapor is present in the gas surrounding the sensor. Under these restrictive conditions, however, it is possible to use the sensor signal to measure the concentration of the specific vapor provided that the sensor was previously calibrated against this vapor.

Persons of ordinary skill in the art of polymer-based condensable-vapor sensors know that a set of different polymers with non-selective vapor absorptances displays a pattern of absorptances that has a degree of selectivity. FIG. 7 illustrates this principle for a set of four different polymers where each polymer is deposited on a different element of an array of four sensor elements. It will be clear to persons skilled in the vapor sensing art that as few as two sensor elements will be useful in some applications whereas more than four sensors will be needed for other applications. Linear or two dimensional arrays are convenient for organizing multiple sensor elements onto a chip when each sensor element is of the same size. On the other hand, layout geometries other than linear and two dimensional arrays might be more convenient or make more efficient use of the chip area under certain conditions, for instance, if the sensor elements are of different sizes.

Each of the four condensable vapor sensor elements 411–422 in FIG. 7 is coated with a different polymer, and it is assumed that the sensor outputs are linearly related to the concentrations of vapors 1 and 2 in the gas surrounding the sensor array. The signal processing/control circuit 430 reads the capacitance of each of the sensor elements 411–422 through the electrical leads 440, and communicates its output to higher level circuits like display drivers or other control circuits through the output bus 450.

Let $S[i,j,k]$ be the sensitivity of sensor $4ij$ to vapor $k$, where $i=1,2, j=1,2$, and $k=1,2$, and, to make the example more concrete, let $k=1$ corresponds to methanol, and $k=2$ corresponds to ethanol. Furthermore, let $C[k]$ be the concentration of the $k^{th}$ vapor in the gas surrounding the four-element sensor array of FIG. 7. Finally, let $V[ij]$ be the measured output signal from sensor element $4ij$, and assume that the values of $S[ij,k]$ are known from previous calibrations of the sensor array. This gives four equations $$V[1,1]=S[1,1,1]C[1]+S[1,1,2]C[2]$$

$$V[1,2]=S[1,2,1]C[1]+S[1,2,2]C[2]$$

$$V[2,1]=S[2,1,1]C[1]+S[2,1,2]C[2]$$

$$V[2,2]=S[2,2,1]C[1]+S[2,2,2]C[2]$$

in the two unknowns $C[1]$ and $C[2]$. Persons of ordinary skill in statistical mathematics know how to use least squares techniques to solve these equations for the most likely values of $C[1]$ and $C[2]$, and how to assign uncertainties to the values of $C[1]$ and $C[2]$ determined in this way. The control/signal processing circuit 430 might be configured to provide the signals V[i,j] on the output bus 450. Alternatively, it might be configured to provide the concentrations C[k] and their uncertainties.

Previous calibration of the S[i,j,k] will have already established expected uncertainties for C[1] and C[2]. If the calculated uncertainties fall within the expected uncertainties, then it can be concluded with some confidence level that only methanol and ethanol are present, and that C[1] and C[2] are their concentrations, respectively. On the other hand, if the calculated uncertainties are much larger than the expected uncertainties, then it is likely that at least one other condensable vapor is present, and that C[1] and C[2] are almost certainly not the respective concentrations of methanol and ethanol.

Persons of ordinary skill in statistical mathematics also know how to

- extend the arguments given above to larger arrays of sensor elements, more vapors, and nonlinear and non-additive relations between the vapor concentrations and sensor-element outputs,
- choose the expected uncertainties to accept a false hypothesis about the vapor composition less than some specified fraction of the time or to reject a true hypothesis about the vapor composition some specified fraction of the time,
- choose different polymers for use on the different sensor elements in such a way as to prevent the matrix of S[i,j,k] from being singular or near singular, or to compensate for the fact that a set of polymers that introduces some singularity into this matrix is being used.

Thus, it is possible to use a set of non-selective sensor elements to produce selectivity over a given set of vapors, and to detect the presence of other vapors that invalidate the measurement. Those of ordinary skill in the art of IC fabrication will also see that different VDP polymers could be applied to different sensor elements of the type of capacitive sensor being described here by using multiple resist lift-off operations. Furthermore, a suitable VDP polymer could be used to protect all of the different dielectric polymers on the different sensor elements as a final deposition step, whether or not any of them were also VDP polymers.

Temperature scanning for selectivity

FIG. 8 shows a substrate 500 suspended over a pit 504 in a silicon chip 502. The substrate 500 is made from a thermal oxide 501 on the top surface of the chip 502. Paramesarwen et al. describe how to design a precursor for a suspended substrate for fabrication at a commercial CMOS foundry, and how to use a maskless anisotropic etch following fabrication of the precursor to micromachine a closed pit under a substrate, thereby creating a suspended substrate. Such a pit is a closed.

Since this type of pit is etched from the front of the chip, the suspended substrate cannot completely cover the pit. If there is only one opening in a suspended substrate over a pit in a silicon chip, then the suspended substrate is a cantilever. Those of ordinary skill in the art of silicon micromachining know that it is possible to use $XeF_2$ to etch a hemispherical pit through a small circular opening to create a ring-shaped suspended substrate surrounding the opening. Even this shape suspended substrate is a cantilever according to the above definition. If there is more than one opening in a suspended substrate over a pit in a silicon chip, then the suspended substrate is a bridge. According to this definition, a suspended substrate in the shape of a tramboline is just an elaborate bridge.

Those of ordinary skill in the art of silicon micromachining know how to etch a pit from the rear of the chip up to the suspended substrate. Such a pit is open. It is possible to create suspended substrates that have no openings over the pit with this type of etching, but openings can be provided if desired. If there is no opening in a suspended substrate over a pit, then the suspended substrate is a membrane. According to these definitions any suspended substrate must be either a membrane, a cantilever, or a bridge, and all pits under suspended substrates, even if produced by a micromachining process other than etching, are either closed or open.

Parameswaren et al. also show how to co-integrate heaters onto suspended substrates, and that it is possible to heat the resulting structures to incandescence while maintaining the rest of the chip at room temperature. Parameswaren et al. further show that the temperature of the heater can be determined from the temperature coefficient of the heater material.

Figure 9:
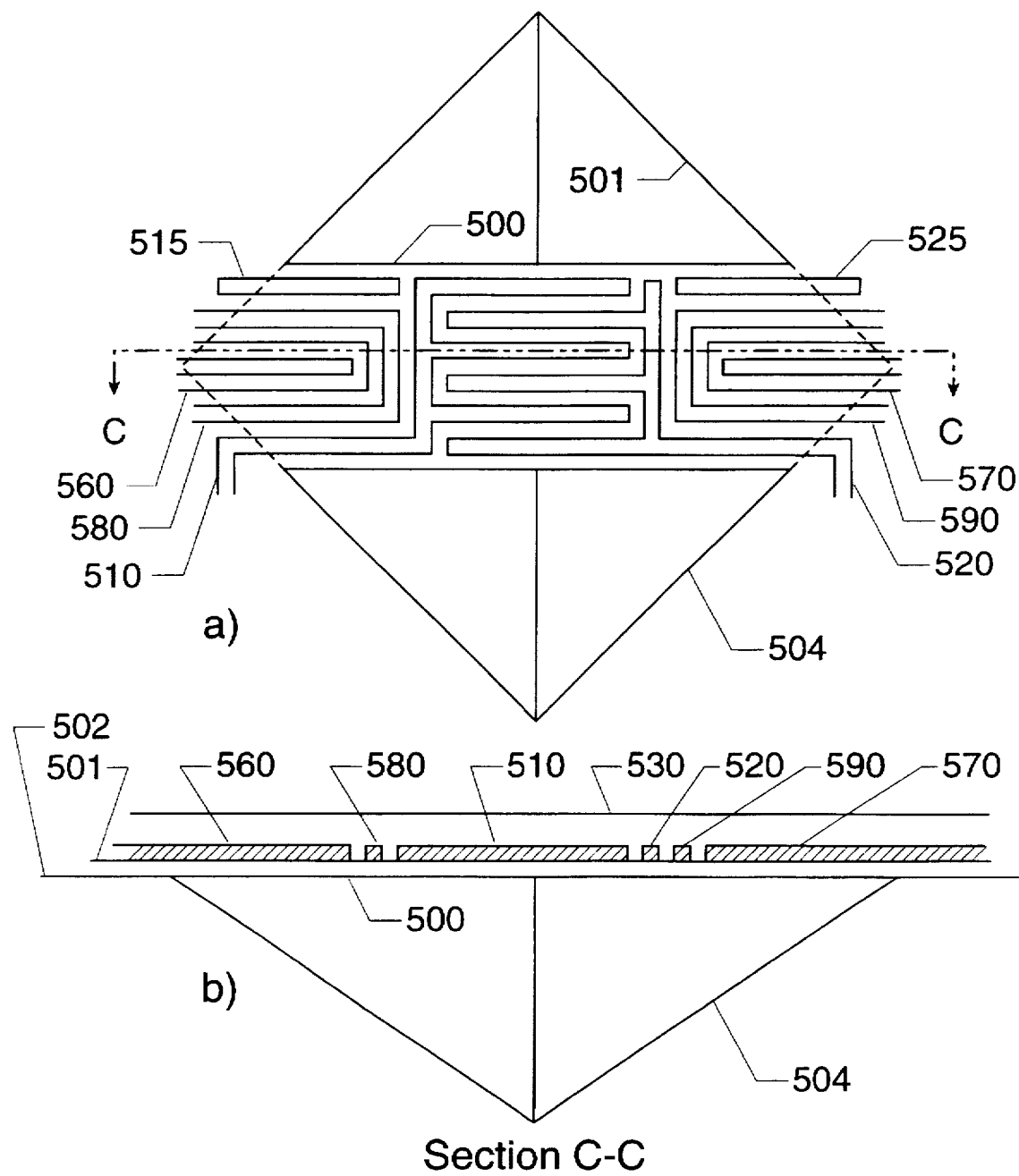

FIGS. 9 and 9b show a top view and a cross section along line C of a preferred embodiment of a condensable-vapor sensor that is co-integrated along with a heater onto the suspended substrate 500 shown in FIG. 8. This structure can be used to distinguish among different vapors according to their different boiling points. The electrodes 515 and 525 serve no electrical purpose. Instead they make the heat transfer through the suspended substrate 500 to the silicon chip 502 more symmetric when electrical currents are passed through the heaters 560 and 570.

Electrical currents are passed through the two electrical heaters 560 and 570 to heat the thermally isolated suspended substrate 500, the pair of interdigitated electrodes 510 and 520, and the vapor-sensitive polymer coating 530. The temperature of the vapor-sensitive polymer coating 530 is determined by measuring the resistances of the temperature sensors 580 and 590 which change approximately linearly with temperature.

Those of ordinary skill in the art of CMOS foundry micromachining will know how to design precursors for the structure shown in FIGS. 9a and 9b or more complex structures involving separate heaters and temperature sensors using the layers provided by any standard IC foundry process. These same people will also see that vacuum-deposition polymerization (VDP) is a process particularly well suited for depositing a uniform coating onto a thermally isolated suspended structure without risking damaging the structure.

If a VDP polymer is used to coat the structure shown in FIGS. 9a and 9b it will coat not only the top surface of the suspended substrate 500, but also the bottom surface and the sides of the etch pit 504 as well as any other exposed portions of the chip 502 on which the substrate is located. (To simplify FIG. 9b, these layers are not shown; only the layer acting as a vapor-sensitive capacitor dielectric is shown.) This means that in the case of suspended substrates, it is not necessary for the substrate to be below the pair of electrodes. The sensor will work just as well if the electrodes are below the substrate as above it, provided only that the substrate supports the electrodes to maintain their spacing and relative orientation.

When no current is flowing through heaters 560 and 570, the temperature of the thermally isolated structure including the polymer layer 530 reaches the same temperature as the chip within a few milliseconds. Vapors having a boiling point greater than the chip temperature are absorbed in the polymer layer 530 and eventually reach an equilibrium concentration in the polymer layer 530 that is proportional to their concentration in the gas surrounding the chip. This changes the capacitance between the pair of electrodes 510 and 520 from its value when no vapors are absorbed in the polymer layer 530.

As the current flowing in the heaters 560 and 570 is increased, the temperature of the suspended structure including the polymer layer 530 increases, and absorbed vapors having boiling points below the instantaneous temperature of the polymer layer are desorbed. The capacitance between the pair of electrodes 510 and 520 changes as the vapors are desorbed. The temperature at which a detectable capacitance change occurs identifies the desorbed vapor (or at least limits its composition to a few vapors having similar or identical boiling points). The difference in capacitance before and after the desorption event is used to calculate the concentration of the vapor in the gas surrounding the chip. The increase in heater current continues until some predetermined temperature is reached, at which point the current is decreased back to zero. This process is called temperature scanning.

Those of ordinary skill in the art of electronics are able to design circuits to deliver a time-varying current to the heaters 560 and 570 while measuring their resistance. For instance, separate current and voltage leads to the heater can be used. Such people will appreciate that it is also possible to reduce the current in the heaters 560 and 570 slowly in order to detect and measure absorption events as well as or instead of desorption events. Those of ordinary skill in the art of condensable-vapor sensors will understand that absorption events may take longer than desorption events, and that the length of the absorption and desorption events may differ from polymer to polymer even for vapors having the same boiling points, thereby providing a means to distinguish between these vapors. Such people will also see that this type of sensor will not be capable of accurately measuring the concentrations of all of the vapors in a complex mixture of unknown vapors. On the other hand, such people will see that it is possible to calibrate this type of sensor to accurately measure the concentrations under less demanding circumstances. For instance, if all of the vapors that can possibly be present in the gas are known, if none of the vapors have very similar boiling points, then this type of sensor will work quite well. Furthermore, this is the case even if the presence of some of the vapors changes the calibration constants for other vapors, provided that the non-additivity among the different vapors has been calibrated.

Note that the heaters 560 and 570 are located between the edges of the etch pit 504, which is shown dashed under the suspended structure in FIG. 9a, and the interdigitated portion of the pair of electrodes 510 and 520. This is different than the location used by Parameswaran et al., Semancik et al., and Cavicchi et al., who locate the heater in the center of the suspended substrate, which is the location of the interdigitated portion of the pair of electrodes in FIG. 9a. The presence of the interdigitated electrodes at the center of the suspended substrate would not necessarily interfere with putting the heater in the same location because the interdigitated electrodes are located on the top surface of the suspended substrate, and the heaters could be encapsulated within the suspended structure.

However, with the layer thicknesses and minimum electrode widths that are currently available from commercial IC-foundry fabrication processes, the heat loss by conduction through the electrode leads, heater leads, and substrate is much larger than that by radiation and air conduction from the surface of the substrate. As a result, only a small fraction of the heat generated in the heaters needs to be delivered to the interior of the region covered by the pair of interdigitated electrodes in order to maintain it at a uniform temperature. Therefore the heater configuration shown in FIG. 9a results in much smaller variations of temperature over the interdigitated portion of the electrodes than over the remainder of the electrodes. This would not be the case if the majority of the heater resistance were located under the interdigitated portion of the electrodes as taught by Parameswaran et al., Semancik et al., and Cavicchi et al.

The temperature variation over the region covered by the pair of interdigitated electrodes can be further minimized by varying the width of the region where the heaters run from one side of the suspended substrate to the other in a direction perpendicular to that of the interdigitated electrode segments. The optimum width for any given operating temperature can be determined from computer simulations of the temperature distribution based on the measured thermal properties of the various layers, the dimensions of all of the structures on all of the layers, and the dimensions of the etch pit.

Consider removing material from the center of the bridge-type suspended substrate shown in FIG. 8 to create two cantilevers with an open space between them. It is possible to design a sensor precursor following the procedures of Parameswaran et al. to suspend the interdigitated portion of the electrode pair between these two cantilevers. Note, however, that the resulting structure will be more fragile than that shown in FIGS. 9a and 9b. The point is that suspended substrates can support other structures like a pair of capacitive electrodes without making contact with them along their entire length.

A final advantage of suspended substrates is that the capacitance from an interdigitated-electrode capacitor to the silicon chip on which it is fabricated is greatly reduced if the capacitor is located on a suspended substrate.

Arrays of temperature-scanning vapor-sensor elements

An alternate preferred embodiment of the condensable-vapor sensor shown in FIG. 7 can be fabricated and post-processed to have an array of suspended substrates co-integrated with a signal processing circuit, where each suspended substrate has a heater, a temperature sensor, and a pair of surface-type capacitor electrodes located on it. In this case, it will be possible to deposit a different polyxylylene polymer on each of the four different sensor elements 411, 412, 421, and 422 without use of any masks or other films such as photoresists.

To see this, first consider a single packaged chip that is mounted in a jig having power and interface circuitry to communicate with the on-chip control/signal-processing circuit 430. The jig is mounted on the condensation stage 55 in FIG. 2, and a sequence of VDP reactions is carried out using the substrate heaters to heat different combinations of the suspended sensor elements 411, 421, 412, 422 to different temperatures during the sequence as follows:

Poly(p-tetrafluoroxylylene) is deposited everywhere (including the suspended sensor element 411) except on the suspended sensor elements 421, 412, and 422. This is accomplished by maintaining the packaged chip, including the suspended sensor element 411, at room temperature on the condensation stage 55 during a poly(p-tetrafluoroxylylene) VDP process, while the suspended sensor elements 421, 412, and 422 are heated to a temperature that is high enough to prevent poly(ptetrafluoroxylylene) from depositing on them.

Poly(p-dichloroxylylene) is deposited everywhere (including the suspended sensor element 421) except for the suspended sensor elements 411, 412, and 422: The packaged chip, including the suspended sensor-element 421, is maintained at room temperature, during a poly(pdichloroxylylene) VDP process, while the suspended sensor elements 411, 412, and 422 are heated to a little more than 130° C., which is high enough to prevent poly(p-dichloroxylylene) from depositing on them while causing negligible thermal degradation to the poly(p-tetrafluoroxylylene) layer already deposited on the suspended sensor element 411.

Poly(p-chloroxylylene) is deposited everywhere (including the suspended sensor element 412) except for the suspended sensor elements 411, 421, and 422: The packaged chip, including the suspended sensor element 412, is maintained at room temperature, during a poly(pchloroxylylene) VDP process, while the suspended sensor elements 411, 421, and 422 are heated to a little more than 90° C., which is high enough to prevent poly(p-chloroxylylene) from depositing on them while causing negligible thermal degradation to the poly(p-dichloroxylylene) layer already deposited on the suspended sensor element 421 and the poly (ptetrafluoroxylylene) layer already deposited on the suspended sensor element 411.

Poly(p-xylylene) is deposited everywhere (including the suspended sensor element 422) except for the suspended sensor elements 411, 421, and 412: The packaged chip, including the suspended sensor element 422, is maintained at room temperature, during a poly(p-xylylene) VDP process, while the suspended sensor elements 411, 421, and 412 are heated to a little more than 30° C., which is high enough to prevent poly (pxylylene) from depositing on them while causing negligible thermal degradation to the poly(p-chloroxylylene) layer already deposited on the suspended sensor element 412 and the poly(p-tetrafluoroxylylene) and poly(p-dichloroxylylene) layers already deposited on the suspended sensor elements 411 and 421, respectively.

In this way, the suspended sensor element 411 is coated with a layer of poly(p-tetrafluoroxylylene).

the suspended sensor element 421 is coated with a layer of poly(p-dichloroxylylene), the suspended sensor element 412 is coated with a layer of poly(p-chloroxylylene), the suspended sensor element 422 is coated with a layer of poly(p-xylylene).

This is a particularly useful result because the cost of the VDP process just described will be independent of how many chips are mounted in the interface/control jig. Therefore, a large number of chips can be processed at one time to share the cost of the VDP processing among all of them, resulting in a very low cost per chip. This means that a very selective condensable-vapor sensor can be obtained with very simple and inexpensive postprocessing: a maskless etch to free the suspended substrates followed by maskless depositions of different polymers using conventional VDP on a large number of packaged chip mounted in an inexpensive jig. Furthermore, if a $XeF_2$ etch is used to suspend the substrates, the etch can be carried out on the packaged chips while mounted in the same jig that will later hold them during the VDP deposition, and they can be kept in the jig between these two post processes. The same jig could also be used for testing the chips before VDP and for batch-mode calibration of the packaged sensor chips if needed following the VDP deposition. This amortizes the cost of the jig and the cost of mounting the packages in the jig and removing them from the jig over three different operations to minimize the overall cost of post-processing and calibration. Finally, until the chips are mounted in the jig they can be fabricated, packaged, and wirebonded with standard commercial IC processes.

To appreciate the power of this type of sensor array consider the following scenario: During normal operation, the sensor elements 411, 421, 412, and 422 are run without heating, and the sensor output signals are processed as described in connection with the description of operation involving FIG. 7. This minimizes the power used by the sensor during normal operation. Periodically, or whenever an unexpected pattern of output signals over the array or an overly large standard deviation is encountered in the data reduction, the temperature of one or more of the sensor elements is scanned and the output recorded. The temperatures at which desorption events are detected are then recorded and compared with a table of boiling points of vapors to identify the vapors making up the gas mixture.

If the mixture is simple enough to be monitored by the array during normal operation, then the calibration constants for the vapors just identified are used and normal operation resumes. If the mixture of vapors is too complex to be monitored by the array during normal operation, then temperature scans are carried out periodically until the mixture changes to one that can be monitored by the normal mode of operation, at which time the normal mode of operation resumes.

Summary, Ramifications, and Scope

Accordingly, the reader will see that the precursors for the condensable-vapor sensors of this invention, which employ polyxylylene polymers as vapor-sensitive dielectric layers or as protective layers, can be manufactured very inexpensively at standard silicon IC foundries. The resulting sensor precursors can then be inexpensively post-processed into final form by vapor deposition polymerization of one or more layers of a polyxylylene polymer or by a maskless etch, or both.

More specifically, polyxylylene polymers convey the following advantages to the dielectric layer of the vapor sensors of this invention:

- no chemical change during long-term exposure to water or high humidity, which eliminates the possibility of degradation of the dielectric layer in humidity sensing and other water-intensive applications
- low water-absorption capacity, which eliminates or minimizes non-linearites and hysteresis in humidity sensing applications
- insolubility in organic solvents below 150° Celsius, which minimizes the possibility of degradation during long term exposure to solvents or the vapors of such solvents In addition, polyxylylene polymers convey the following advantages as protective layers in the vapor sensors of this invention:

- conformal, pinhole-free layers thin enough to have negligible effect on the sensitivity and time constant of a sensor employing another polymer as the vapor-sensitive dielectric, and to permit wirebonding through the protective layer, replacement of the degradation-prone region near the air-dielectric interface with a layer that is much more resistant to degradation under prolonged exposure to water and organic solvents and vapors, coverage of the humidity-sensitive surfaces that are in direct electrical contact with a field concentrator by a layer that prevents surface conduction to the field concentrator.

coverage of the condensation-prone air/field-concentrator interface by a layer that prevents condensation on the field concentrator, Co-integration of a pair of capacitive electrodes on a suspended substrate reduces the stray capacitance from the electrodes to the silicon chip. Furthermore, co-integration of a pair of capacitive electrodes, a vapor-sensitive dielectric, a heater, and a temperature sensor onto a suspended substrate conveys the following advantages to the condensable-vapor sensors of this invention:

the temperature at which different vapors absorb and desorb can be used to distinguish among the different vapors, the temperature range over which different vapors absorb and desorb can be used to distinguish among different vapors having the same or similar absorption and desorption temperatures, the time that it takes different vapors to absorb or desorb at a fixed temperature can be used to distinguish among different vapors having the same or similar absorption and desorption temperatures, the temperature of the suspended substrate can be raised during postprocessing to prevent or facilitate the deposition of various layers on the suspended substrate.

The reader will further see that polyxylylene polymers are well suited for use on variable-temperature suspended substrates as well as on substrates that are thermally sinked to the chip temperature. They are also well suited for use with arrays of sensor elements having different dielectric polymers, either as one of many dielectric polymers, or as protective coatings for all of the dielectric polymers. Indeed, arrays of sensor elements comprising variable temperature substrates coated with different polyxylylene polymers combine low cost fabrication with a hierarchy of operational modes that trade power dissipation against selectivity, and provide considerable selectivity in the most complex and power-intensive modes of operation.

Specifically, this type of sensor can monitor the concentration of a particular vapor species such as relative humidity. It will also be able to report the concentrations of anticipated interfering vapors and any additional uncertainties that these introduce into the reported concentration of the monitored species. Furthermore, it will also be able to report when its output is invalid due to interferences from unexpected or unknown vapors, yet it should be very inexpensive to manufacture in volume.

Finally, a few ramifications of the above-stated advantages require explicit mention here.

Protection of a dielectric layer of high water-absorption capacity with a low water-absorption polyxylylene layer allows benefits of the high water-absorption layer to be derived while reducing or eliminating many of the worst problems associated with the use of this type of dielectric.

All of the discussions about deposition that were given in terms of polyxylylene polymers apply equally well to any other polymer that can be deposited by VDP.

The physical and chemical properties of any other polymer that can be deposited by VDP will determine the suitability of that polymer for use as a condensable-vapor sensitive dielectric in any particular application.

I claim:

1. A condensable-vapor sensor of the surface-capacitor type, comprising
   (a) an electrically insulating substrate,
   (b) a pair of electrodes situated on said electrically insulating substrate, said pair of electrodes being selected from the group of pairs of interdigitated electrodes, pairs of spiral electrodes, and combinations of said pairs of electrodes,
   (c) a dielectric layer in functional relationship with said pair of electrodes,
   wherein said dielectric layer is a polyxylylene polymer.

2. The condensable-vapor sensor of claim 1 further including circuit means in operational relationship with said condensable-vapor sensor for measuring an electrical quantity that depends upon the capacitance between said pair of electrodes, wherein said condensable-vapor sensor and said circuit means are co-integrated on an integrated-circuit chip.

3. An array of condensable-vapor sensors comprising
   (a) a first condensable-vapor sensor as recited in claim 1,
   (b) a second condensable-vapor sensor as recited in claim 1,
   wherein said first condensable-vapor sensor and said second condensable-vapor sensor are co-integrated on a single integrated-circuit chip.

4. A condensable-vapor sensor of the surface-capacitor type, comprising
   (a) an electrically insulating substrate,
   (b) a pair of electrodes situated on said electrically insulating substrate, said pair of electrodes being selected from the group consisting of pairs of interdigitated electrodes, pairs of spiral electrodes, and combinations of said pairs of interdigitated electrodes and said pairs of spiral electrodes,
   (c) a dielectric layer in functional relationship with said pair of electrodes,
   (d) a protective layer in functional relationship with said dielectric layer, said protective layer being located on the same side of said electrically insulating substrate as said dielectric layer,
   wherein said protective layer is a vapor deposition polymer.

5. The condensable-vapor sensor of claim 4 wherein said vapor deposition polymer is a polyxylylene polymer.

6. The condensable-vapor sensor of claim 4 further including circuit means in operational relationship with said condensable-vapor sensor for measuring an electrical quantity that depends upon the capacitance between said pair of electrodes, wherein said condensable-vapor sensor and said circuit means are co-integrated on an integrated-circuit chip.

7. The condensable-vapor sensor of 4 further including a field concentrator between said dielectric layer and said protective layer.

8. An array of condensable-vapor sensors comprising
   (a) a first condensable-vapor sensor as recited in claim 4,
   (b) a second condensable-vapor sensor as recited in claim 4,
   wherein said first condensable-vapor sensor and said second condensable-vapor sensor are co-integrated on a single integrated-circuit chip.

9. A condensable-vapor sensor of the surface-capacitor type, comprising (a) an integrated-circuit chip defining a pit, (b) an electrically insulating substrate supported by said integrated circuit chip, said electrically insulating substrate being suspended over said pit, (c) a pair of electrodes supported by said electrically insulating substrate, said pair of electrodes being selected from the group consisting of pairs of interdigitated electrodes, pairs of spiral electrodes, and combinations of said pairs of interdigitated electrodes and said pairs of spiral electrodes, (d) a dielectric layer in functional relationship with said pair of electrodes, wherein said dielectric layer is a vapor deposition polymer.

10. The condensable vapor sensor of claim 9, wherein said vapor deposition polymer is a polyxylylene polymer.

11. The condensable-vapor sensor of claim 9, wherein said pit is closed.

12. The condensable-vapor sensor of claim 9, wherein said pit is open.

13. The condensable-vapor sensor of claim 9, wherein said electrically insulating substrate is selected from the group consisting of membranes, cantilevers, and bridges.

14. The condensable-vapor sensor of claim 9 further including circuit means in operational relationship with said condensable-vapor sensor for measuring an electrical quantity that depends upon the capacitance between said pair of electrodes, wherein said condensable-vapor sensor and said circuit means are co-integrated on said integrated-circuit chip.

15. The condensable-vapor sensor of 9 further including a temperature sensor supported by said electrically insulating substrate.

16. The condensable-vapor sensor of 9 further including a heater supported by said electrically insulating substrate.

17. An array of condensable-vapor sensors comprising (a) a first condensable-vapor sensor as recited in claim 16, (b) a second condensable-vapor sensor as recited in claim 16, wherein said first condensable-vapor sensor and said second condensable-vapor sensor are co-integrated on a single integrated-circuit chip.

18. The array of condensable-vapor sensors of claim 17, wherein said dielectric layer of said first condensable-vapor sensor is a vapor deposition polymer.

19. The array of condensable-vapor sensors of claim 18, wherein said vapor deposition polymer is a polyxylylene polymer.

* * * * *